May 13, 1958 O. R. BRISTOW Plant Pat. 1,701
AZALEA PLANT
Filed Dec. 19, 1956
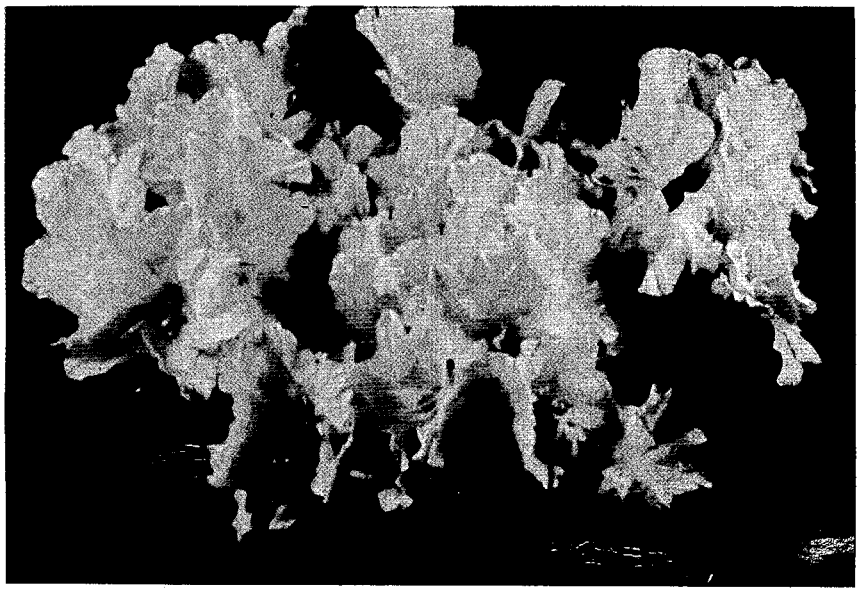
INVENTOR-
OWEN R. BRISTOW
Orville R. Seidner
AGENT United States Patent Office Plant Pat. 1,701

Patented May 13, 1958

1,701

AZALEA PLANT

Owen R. Bristow, San Bernardino, Calif., assignor to Mossholder Nursery, Orange County, Calif.

Application December 19, 1956, Serial No. 629,429

1 Claim. (Cl. 47—60)

This invention relates to a distinct and new variety of azalea plant reproduced as a result of deliberate experiments in hybridization carried out at my nursery in San Bernardino, California, the plant being derived from a cross-breeding of unpatented plants numbered 109B and 42 in my breeding records.

My distinct and new variety was immediately recognized as having particularly valuable commercial qualities for either natural outdoor planting or for greenhouse forcing under glass. It was found to be unusually vigorous in rooting from cuttings. Furthermore, it required very little feathering during the forcing period, thus reducing very materially the grower's labor and experience from that usually required by known varieties.

It was further found that forcing was readily controlled in this variety, in that the plant could be made to bloom profusely for the Christmas season, for Valentine Day, for Easter, or for any desired intermediate period.

Other distinguishing characteristics over known varieties were found in the exceptional bud setting and fast growing qualities. The plant has, for example, the growing qualities of the Rutherfordiana strain accompanied by better flowering size than many of the varieties of the Belgium Indica strain. The buds set prolifically and firmly erect on the stems.

Asexual reproduction of this distinct and new variety of azalea was accomplished by me at my nursery in San Bernardino, California, by the known method of removing cuttings from the original hybrid plant which matured from a seedling, and potting the cuttings separately from the donor plant. Subsequent reproductions of the plant in the same manner indicate that the foregoing characteristics, as well as further distinguishing characteristics brought forth in the description below, are permanently fixed, and the accompanying illustration of a forced cutting in bloom shows the prolific blooming and striking color of the flowers.

The following is a detailed specification of the plant and flower, reference being had to the British Horticultural Chart of the British Colour Council for color indentification:

*Plant*

Form of plant: Bushy and compact; usually somewhat uniformly broader than its height.

Growth habit: Moderately fast; somewhat similar to Rutherfordiana. Sets buds quite prolifically, with bud setting easily controlled for early or late in blooming season according to pruning practice.

Rooting: Roots easily and vigorously from cuttings with less mortatity of the young plants than is usual with known varieties; grows strongly on its own roots.

Blooming habit: Prolific both outdoors and under glass. When in full bloom, the foliage is substantially completely hidden by the flowers.

Blooming season: From late March through April for natural outdoor plantings. Very easily forced in greenhouse planting to bloom at least as early as mid-December. Requires little or no suckering or feathering during the forcing period under normal conditions.

*Foliage*

Size: Mature leaves average from 1¼″ to 2″ in length and ½″ to ⅞″ in width.

Quantity: Abundant.

Color: New foliage, upper and lower sides light green. Old foliage, upper side glossy deep green, under side light green.

Shape: Oval and slightly pointed.

Texture: Normal on both upper and lower sides.

Edge or margin: Smooth.

Ribs and veins: Normal.

Aspect: General appearance of plant somewhat resembles Professor Walters variety, except for bushy growth and denser foliage.

*Flower*

Size: 3″ to 4″ across flower.

Flowers borne: 2 to 4 on each stem.

Quantity of bloom: Abundant in outdoor blooming as well as when forced.

Continuity: Lasting quality similar to Rutherfordiana and better than most Belgium Indica species.

Petalage:

*Size.*—2½″ to 2¾″ long and mostly 1½″ in width with only a few less than that; quite generally uniform.

*Number of petals under normal conditions.*—7.

*Color of bud.*—Slightly darker at the base of the bud than that of the open flower, shading to a tip of lighter shade than the flower.

*Color of open flower.*—Principal color per Plate $022/_2$ with lighter shades of this color throughout the flower, with speckling per Plate $862/_2$ from the throat of the flower to within ½″ of the tip of the petals at the top half of the flower.

Appearance: Forcing results in deeper shade of the same color than when grown naturally. The illustration shows substantially the color of the forced flower.

Shape: Petals are deeply ribbed on the underside, extending from the sepal outwardly to within about 1″ of the tip. Ribbed portions are generally of lighter shade than the flower. Ribbed portions appear to strengthen flower and contribute to lasting qualities of the blooms. When in full bloom, the large quantity of crowded flowers results in a very attractive ruffling of the petals.

Arrangement: Multi-flowering on each stem.

Persistence: Sets buds regularly every year, and in southern California will flower lightly outdoors from October to the heavy spring blooming period. But if trimmed back in July, for example, can be grown to force at any time from mid-December to Easter.

*Reproductive organs*

Stamens: 11 to 16 per flower.

*Anther.*—Normal, pale yellow.

*Filament.*—Normal, pale pink.

Pollen: Normal, pale yellow.

Styles: Creamy white. Stigma—color per Plate $861/_3$.

Ovary: Normal.

Having illustrated and described the invention, what is claimed as new and patentable is:

A distinct and new variety of azalea plant, substantially as illustrated and described hereinabove characterized generally by its firm rooting and unusual controllable forcing qualities as well as adaptability to outdoor growth, its compactness of plant with prolific bud setting qualities, and particularly characterized by its massive blooming of large deeply ribbed flowers having characteristic speckling on the top half of the flower.

No references cited.